United States Patent [19]

Olsen

[11] Patent Number: 5,496,297
[45] Date of Patent: Mar. 5, 1996

[54] OSTOMY COUPLING

[75] Inventor: Hans Olsen, Bronshoj, Denmark

[73] Assignee: Coloplast A/S, Denmark

[21] Appl. No.: 199,547

[22] Filed: Feb. 22, 1994

[30] Foreign Application Priority Data

Feb. 22, 1993 [DK] Denmark .................. 0197/93

[51] Int. Cl.[6] ...................................... A61F 5/48
[52] U.S. Cl. ............................ 604/339; 604/338
[58] Field of Search ...................... 604/338, 339, 604/341–344

[56] References Cited

U.S. PATENT DOCUMENTS

| 4,664,661 | 5/1987 | Ferguson . |
| 4,929,245 | 5/1990 | Holtermann ............ 604/338 |

FOREIGN PATENT DOCUMENTS

| 153122 | 6/1988 | Denmark . |
| 286501 | 10/1988 | European Pat. Off. . |
| 0347025 | 12/1989 | European Pat. Off. . |
| 2193098 | 2/1988 | United Kingdom . |
| 2215212 | 9/1989 | United Kingdom . |
| 9101119 | 2/1991 | WIPO ................ 604/338 |
| 9101118 | 2/1991 | WIPO ................ 604/338 |
| 9318725 | 9/1993 | WIPO . |

Primary Examiner—Randall L. Green
Assistant Examiner—Mark O. Polutta
Attorney, Agent, or Firm—Ostrolenk, Faber, Gerb & Soffen

[57] ABSTRACT

An ostomy coupling including two annular coupling parts and a locking ring. Each coupling part is attached to one of an adhesive disc, or a collection receptacle or a closing plug. The first coupling part has a collar with a radially outwardly projecting annular edge. The edge forms a groove with an in the radial direction innermost groove section. An annular recess is positioned in the radial direction inner side of the collar. The second coupling part has an axially projecting part with an annular radially outwardly projecting beak capable of engaging the annular recess in the first coupling part. The locking ring has an annular protrusion that projects inwardly in the radial direction. The locking ring is positioned in the groove of the first coupling part, so that its innermost diameter when it is in its locked position, is smaller than the largest beak diameter of the second coupling ring, and the annular recess of the first coupling part is closer to the attachment surface of this coupling part to the collection receptacle, the closing plug or the adhesive disc than the annular innermost groove section.

18 Claims, 4 Drawing Sheets

5,496,297

OSTOMY COUPLING

BACKGROUND OF THE INVENTION

1. Field of the Invention

The present invention relates to an ostomy coupling of the kind comprising a first and a second annular coupling part and a locking ring, where one of the coupling parts is secured to a self-adhesive plate or disc by which it is attachable to the ostomy patient around his stoma, and where the other coupling part carries a collection receptacle or closing plug, and where the locking ring is intended for holding together the first and the second coupling part in tight and secure contact with each other.

2. Description of Related Art

In the following an ostomy patient or ostomist means a person who has a colostomy, an ileostomy or an urostomy. In such persons a projection of the colon, ileum or urethra has been performed surgically, so that the body's waste products passing through these organs are discharged through an artificial opening, and are collected continuously or at intervals in a collection receptacle, such as a foil bag. If the collection is performed at intervals, the collection receptacle may in the intervening periods be replaced by a closing plug, as known e.g. from DK patent specification No. 153 122.

The collection bag or the closing plug may be attached directly around the stoma by means of an adhesive disc, but since these parts must be changed even several times daily, and since frequent removal of such an adhesive disc from the skin may cause extreme damage thereto, use is generally made of two-part ostomy equipment consisting of an adhesive disc which is attachable around the ostomist's stoma, and on the non-adhesive surface of which an annular coupling part is attached, often called a plate coupling part, which can be coupled to another annular coupling part which carries a collection receptacle or a closing plug.

Since it is extremely important that such ostomy couplings are tight and secure against unintended removal, it calls, however, for quite large axial pressure force to couple them together, and a large axial pulling force to separate them again. Since the skin area around a stoma is often very tender, recent years have seen the development of ostomy couplings which can be coupled together and separated with reduced axial force impacts.

In this connection it should be observed that by axial pressure and pulling forces are meant forces which in the mounting and demounting situation influence the skin area around the stoma with pressure and pull, respectively. Similarly, by statements of axial direction are meant directions which are essentially parallel to the center axis of the coupling parts. The axial thickness of a coupling ring or locking ring thus denotes the distance between two planes which are perpendicular to the center axis and intersect the surface or line on the coupling or locking ring which in a use situation is closest to the user's stoma-surrounding skin surface and remotest from the user's stoma-surrounding skin surface, respectively.

A coupling of the above kind is known e.g. from EP patent specification No. 347 025. The ostomy coupling disclosed therein consists of two annular coupling parts, one of which is attached to an adhesive disc for attachment around a stoma, and the other carries a collection bag, and a locking ring which locks together the two coupling parts. The two coupling parts each have a closed loop-form, i.e. that in their annular extension they stretch a distance in axial direction away from the adhesive disc or the collection bag, respectively, and deflect in radial outward direction. The part on the first and the second coupling part, respectively, which stretches radially outwards, has plane surfaces. In the coupling situation the outer plane surfaces facing away from the adhesive disc and the bag, respectively, to which they are attached, are placed against each other, whereafter they are squeezed together by means of a locking ring having U-shaped cross-section, the locking ring embracing the two radially projecting parts of the coupling parts in their entire annular extension. This ostomy coupling is consequently lockable without any use of axial force impacts, since the two coupling parts are held together by the locking ring alone.

A similar ostomy coupling is known from WO published specifications No. 91/01118 and 91/01119. The ostomy coupling therein disclosed differs from the one mentioned above in having a primary and a secondary coupling mechanism, and in the two coupling parts not having plane contact surfaces. The two coupling parts each have projecting parts being capable of passing into mutual engagement so as to form a primary tight assembly of the coupling parts. This primary coupling together and uncoupling thereof calls for moderate axial pressure and pulling forces. For psychological reasons and in consideration of any extreme load, another locking ring with U-shape is positioned around the coupling part. This locking ring which constitutes the secondary coupling mechanism, embraces the radially projecting parts of the two coupling parts without, however, necessarily having a squeezing effect thereon. The secondary coupling mechanism will thus not be loaded under normal circumstances, but only in case of a substantial pull in the bag part.

The locking rings described above must, however, necessarily have a certain axial thickness, since the locking rings have two annular radially inwardly projecting legs or protrusions for enclosing the annular radially outwardly projecting parts of the two coupling parts. In view of material strength and manufacturing tolerances there is thus a lower limit for the axial thickness of the coupling.

It is of great importance to ostomy patients that the ostomy equipment is as invisible as possible, and that it can be hidden under the clothing. Even the smallest reduction in axial thickness will therefore have great phychological importance.

GB patent specification No. 2 215 212 discloses an ostomy coupling consisting of two coupling parts and a locking ring, which only has one annular radially inwardly projecting protrusion. One of the coupling parts is of a deformable material and is, as described above, attached to an adhesive disc which projects outwardly therefrom in a closed loop-form so as to form a collar having an annular groove. The other annular coupling part is attached to a collection bag and extends outwardly therefrom in axial direction, and is furthermore provided with a small annular beak. The two coupling parts are assembled by one deformable coupling part being positioned in radial direction over the other, so that the beak in the second coupling part engages with an annular recess in the deformable one coupling part. This engagement between the beak and the recess has in itself no significant strength because of the flexible property of the deformable material. The locking ring is thereafter positioned in the annular edge, whereafter it is locked and thereby squeezes the deformable coupling part against the other coupling part.

This last described ostomy coupling may thus be shaped with a smaller axial thickness than ostomy couplings where the locking ring has two annular radially inwardly directed legs or protrusions which in the coupling situation are to embrace and hold or squeeze together radially outwardly projecting parts on the two coupling parts.

The functional basis of the ostomy coupling according to GB patent specification No. 2 215 212 is, as described above, deformation of the coupling material. Such deformation, however, results only in a very small radial engagement and consequently provides only limited strength against unintended tearing off. Even in such cases where the locking ring exerts considerable force on the deformable material, the radial engagement will be very small, and at the same time this will entail that substantial finger strength is required for locking the locking ring.

This is very inexpedient since many ostomy patients are elderly people with little finger strength and/or failing motorics. Furthermore, the force impact of the locking ring on the deformable material will propagate to the in radial direction innermost coupling part, whereby the latter may easily break.

SUMMARY OF THE INVENTION

Thus it is the object of the present invention to provide an ostomy coupling comprising a first and a second annular coupling part and a locking ring for locking together the two coupling parts, where one of the two coupling parts is attached to an adhesive disc and the other of the two coupling parts carries a collection receptacle or a closing plug, the first coupling part comprising a collar with a radially outwardly projecting annular edge for forming a groove having an in radial direction innermost groove section, and an in its in radial direction inner side positioned annular recess, and the second coupling part comprising an axial projecting part with an annular radially outwardly projecting beak being capable of engaging with the annular recess in the first coupling part when the said first coupling part is positioned around the second coupling part, and where the locking ring has an annular in radial direction inwardly projecting protrusion, and that the locking ring is positioned in the groove of the first coupling part, the said ostomy coupling being capable of coupling on and off by use of small or moderate finger strength and simultaneously being safe against unintended removal of the collection receptacle or the closing plug.

This object is achieved by an ostomy coupling of the kind mentioned above, in that the innermost diameter of the locking ring, when it is in its locked position, is smaller than the largest beak diameter of the second coupling ring, and that the annular recess in the in radial direction inner side of the first coupling part in axial direction is closer to the attachment surface of this coupling part to the collection receptacle, the closing plug or the adhesive disc than the annular innermost groove section.

Thus, the coupling ring according to the invention is fairly easy to couple on and off, since the two coupling parts during the coupling together are first coupled together by a primary coupling mechanism, the first coupling part being forced over the second coupling part by use of small or moderate axially directed pressure forces, whereby the annular beak of the second coupling part will engage with the recess in the first coupling part, whereafter the locking ring, which may already be loosely positioned in the groove of the first coupling part without close contact with groove bottom and groove walls, is locked, so that the radially inwardly directed protrusions of the locking ring abut tightly against the bottom and walls of the groove at least in an area, without, however, influencing the first coupling part with appreciable squeeze forces. Thus the locking ring is lockable by application of moderate or slight finger strength.

At loads which try to tear the two coupling parts apart, the first coupling part will be fixedly squeezed between the annular beak of the second coupling part and the radially inwardly projecting protrusions of the locking ring, whereby the coupling strength will increase. This means that loads to which an ostomy coupling according to the invention is exposed in use contribute to increasing the coupling strength and consequently the tightness and safety against unintended removal of the collecting receptacle or the closing plug.

According to a preferred embodiment of the invention the first coupling part is sealed to a collection bag or a closing plug, and the second coupling part is sealed to an adhesive disc. The annular groove in the first coupling part is preferably very narrow in the in radial direction innermost part, i.e. less than 1 mm wide, and expands width-wise in radial outward direction, preferably in one or more steps.

By groove width is meant the distance between the wall surfaces of the groove on a line which is parallel to the center line of the coupling part.

The radially inwardly projecting protrusion of the locking ring is preferably so shaped as to correspond to the in radial direction innermost and narrowest part of the annular groove of the first coupling part.

The sealing surface between the two coupling parts is constituted by the contact between the beak on the second coupling part and the recess in the first coupling part. These parts are preferably so constructed that there is an annular narrow sealing surface enclosed on both sides by annular clearances between the beak and the first coupling part. Hereby a particularly good seal and a reduced demand on the tolerances of the units are obtained. It is particularly preferred that the sealing surface is positioned at a distance from the tip of the beak, and that the sealing surface is thus constituted by the contact between an annular surface area on the recess of the first coupling part and an annular surface area on one of the surfaces of the beak, and that this one of the surfaces of the beak in an area which adjoins the tip of the beak is not in direct contact with the first coupling part.

The annular recess in the first coupling part is preferably so shaped as to have an annular surface which is essentially perpendicular to the center axis and faces the point of attachment of this coupling part to the collection receptacle, the closing plug, or the adhesive disc, and at the same time the beak of the second coupling part is so shaped as to have an annular surface which corresponds to the annular surface of the recess, so that these two surfaces, which are essentially perpendicular to the center axis, abut against each other when the coupling is locked. By this embodiment a particular increase in the coupling strength is achieved when the coupling is exposed to loads which try to tear the coupling parts apart.

Preferably the locking ring is provided with a two-step lock in the way it is disclosed in WO 91/01118. According to a particularly preferred embodiment of the locking ring it is provided with an in radial direction inner spring which extends throughout the entire annular extension of the ring, the locking ring, as seen in section, being curved in the area which projects radially outwards from the annular protrusion. It is especially preferred that the locking ring comprises, as seen in section, an S-shaped segment or intermediate piece. According to this embodiment it is achieved that the dependency of the coupling efficiency on the manufacturing tolerances of the units becomes significantly reduced. Further, the coupling will seem less rigid, it will maintain a good seal even upon wringing and bending the entire coupling in use, and it will consequently be more pleasant for ostomy patients to wear.

The locking ring and the plate coupling part are preferably made of an essentially non-deformable polymeric material. For reasons of production it is particularly advantageous to make the coupling parts and the locking ring by injection molding in a material suited for this purpose.

Before the two coupling parts of the ostomy coupling are coupled together, the locking ring is preferably placed in the groove of the first coupling part in its non-locked position. If the locking ring is provided with a two-step lock as mentioned above, the locking ring may advantageously be positioned in its first locking-position, so that the annular radially inwardly projecting protrusion of the locking ring is not in close contact with the bottom of the groove throughout the entire annular extension of the groove.

When the coupling part is attached around the stoma, the primary coupling mechanism of the coupling is coupled together, whereafter the locking ring which constitutes the secondary coupling mechanism is locked completely.

At coupling off, the locking ring is opened, whereafter the two coupling parts are separated from each other by application of small or moderate pulling forces, a pulling flap preferably being positioned in the coupling part which carries a collection receptacle or a closing plug.

It is especially advantageous that this pulling flap is positioned on the annular collar edge of the coupling part, since by that means it is avoided that the locking ring falls out or is torn out of the groove during removal of the receptacle or plug carrying coupling part.

In the following the invention is explained in more detail, reference being made to the drawings.

DETAILED DESCRIPTION OF PREFERRED EMBODIMENTS

Figure 1:
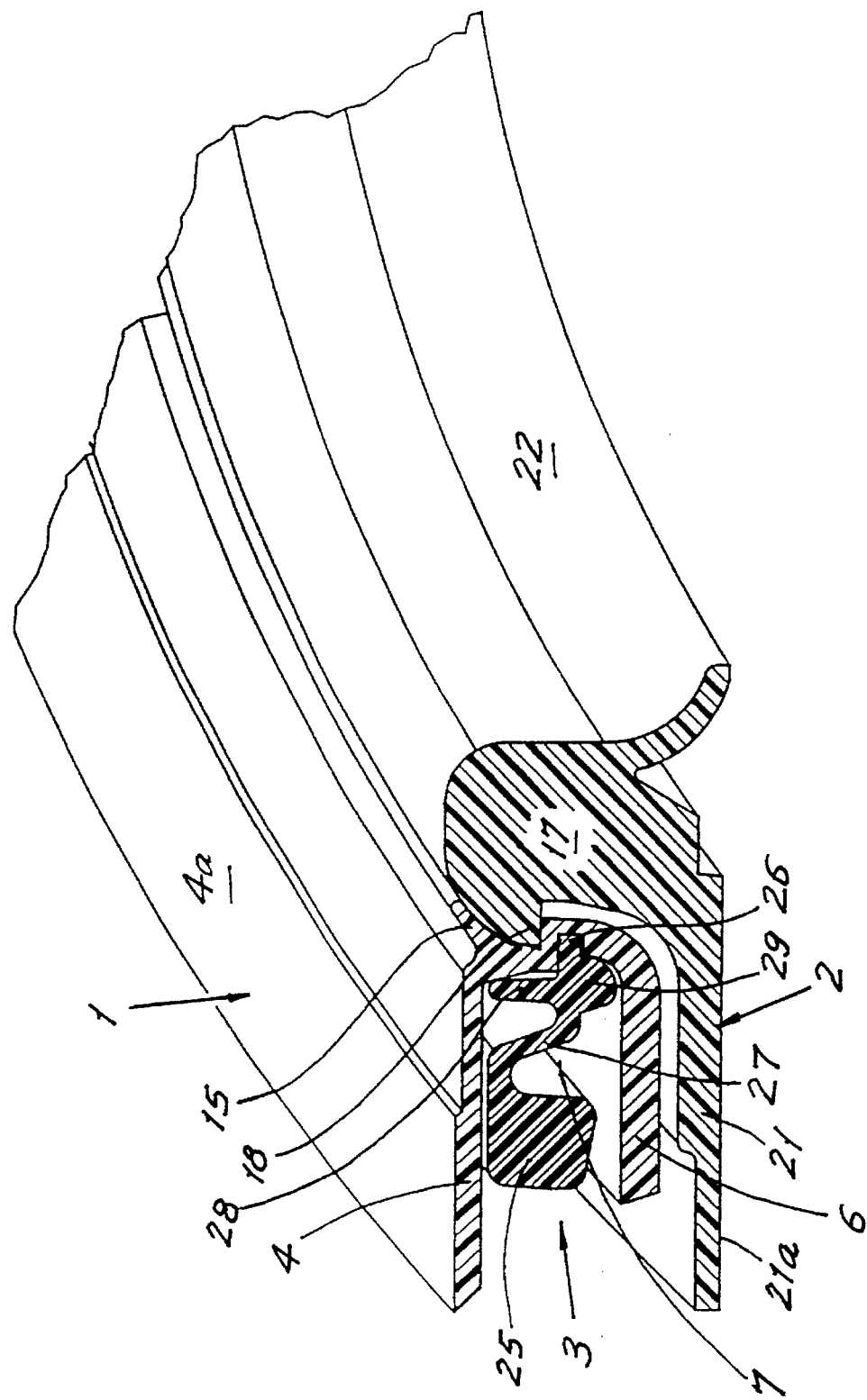
FIG. 1 is a perspective view of a radial section through an embodiment of the ostomy coupling according to the invention in locked state.
Figure 2:
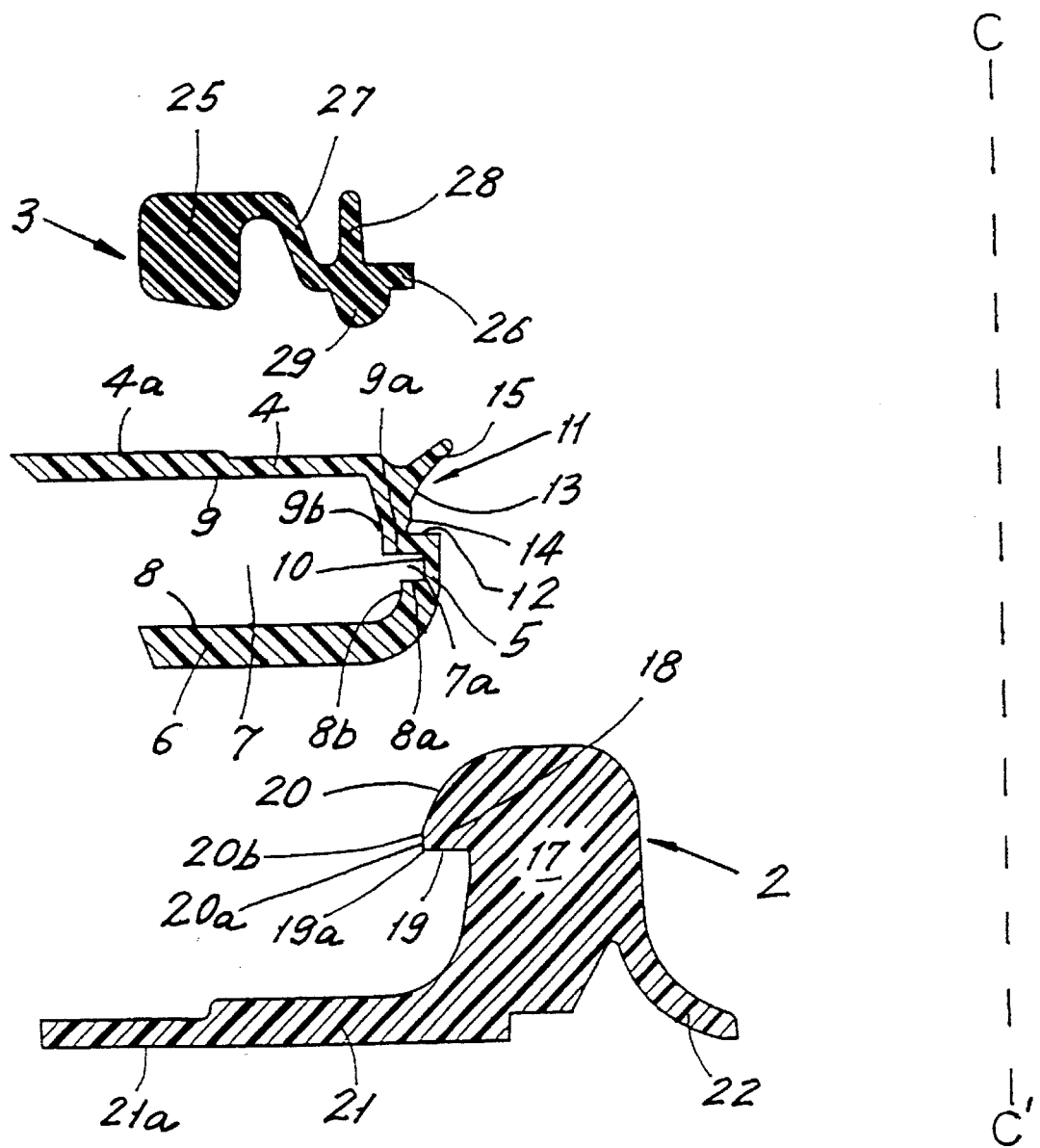
FIG. 2 is a radial section through the locking ring, the first and the second coupling part, respectively, of the ostomy coupling shown in FIG. 1.
Figure 3:
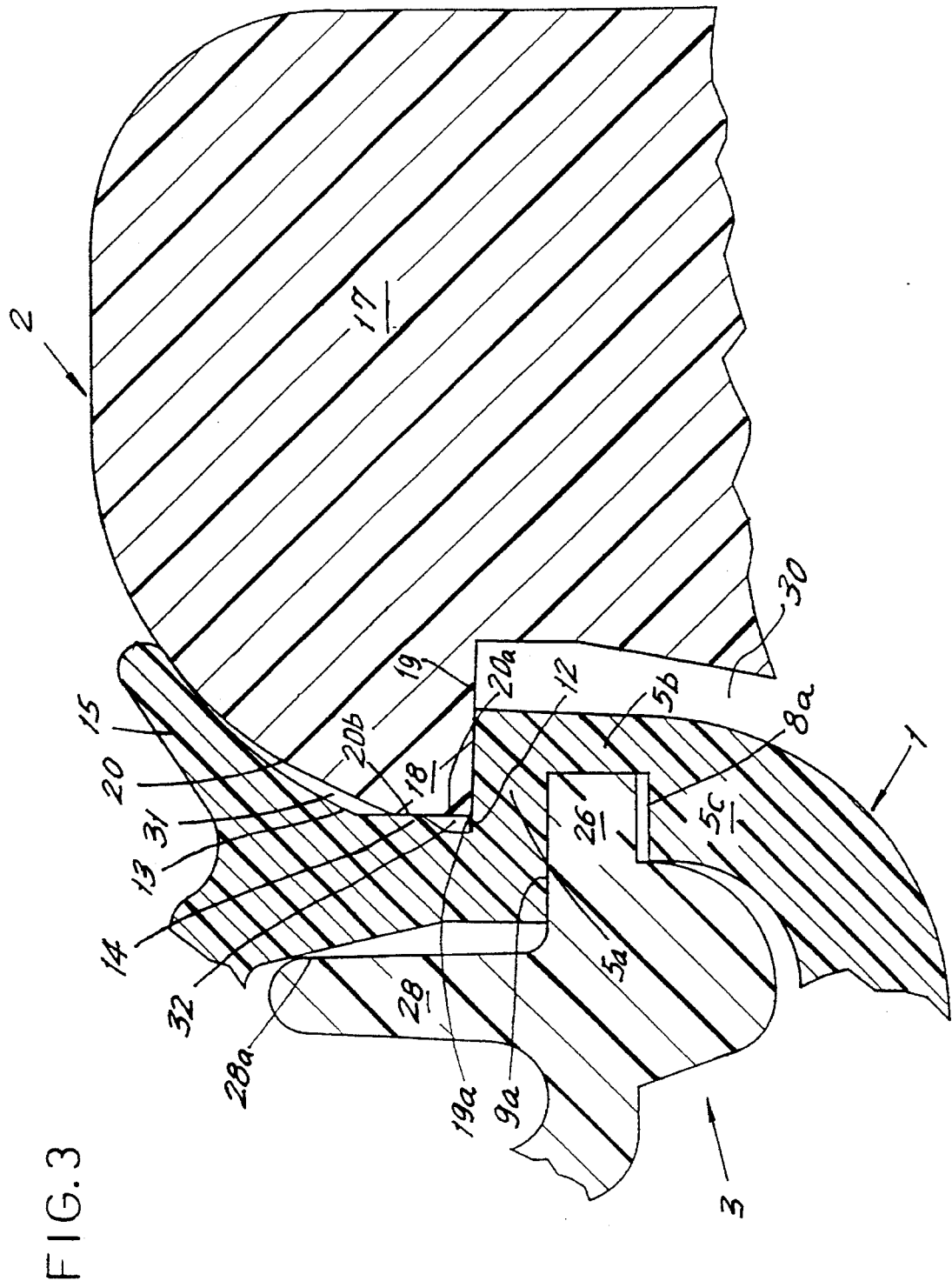
FIG. 3 is a segment of a radial section through the ostomy coupling shown in FIG. 1.

FIGS. 1, 2 and 3 show an especially preferred embodiment of the ostomy coupling according to the invention in mounted and demounted state, respectively. The ostomy coupling comprises a first coupling part 1, a second coupling part 2, and a locking ring 3. The first coupling part 1 carries in a manner known per sea not shown collection receptacle or closing plug being attached e.g. by welding to an annular surface area 4a throughout the entire annular extension of the coupling part. This first coupling part is hereinafter designated the bag coupling part.

The second coupling part 2, hereinafter designated the plate coupling part, is in a manner known per se attached e.g. by welding to a not shown adhesive disc or plate in an annular surface area 21a, by which it can be adhered to the skin area around a stoma.

The bag coupling part 1 comprises a base portion 4 having a collar 5 projecting axially from the base portion 4, the said collar 5 having a radially outwardly projecting annular edge 6 for forming a groove 7. The width of the groove 7 which is defined as the distance between the inner wall surfaces 8 and 9 of the groove, decreases in step 8b, 9b from both side walls 8, 9 in radially inward direction so as to form an in radial direction innermost annular groove section 7a with groove walls 8a and 9a and a groove bottom 10.

In the embodiment shown of the invention the groove width decreases in one step 8b, 9b from the side wall 8 closest to the user and the side wall 9 most remote from the user, respectively, in the situation of use. Of course the groove width may just as well decrease in several steps from each of the two side walls 8, 9, but it is particularly advantageous that the side wall decreases from the side wall precisely in one step 9b, which is explained in more detail below. It is particularly preferred that the step 9b at least in the area closest to the base portion 5 tapers radially inwardly from the base portion 4.

Furthermore, the bag coupling part 1 has a recess 11 in its in radial direction inner side of the collar 5. The recess 11 is so positioned that in axial direction it is closer to the attachment surface 4a of the coupling part to the collection receptacle or the closing plug. The recess 11 has a first essentially plane surface 12 which is essentially perpendicular to the center axis C–C' of the coupling part 1, as indicated in FIG. 2, and a second rounded surface 13 with an annular sealing rib 14. Alternatively the surface 12 may be inclined in relation to the center axis C–C', it however, has to be ensured that the beak of the plate coupling part 2 which is described later on is capable of engaging with the recess 11 with a certain strength. The in radial direction innermost section of the rounded surface 13 further constitutes the wall surface of an annular lip 15 which forms a secondary seal when the coupling parts 1, 2 are coupled together.

In radial elongation of the annular edge 6 of the bag coupling part 1 is further positioned a not shown pulling off flap for removal of the bag coupling part 1 from the plate coupling part 2.

The plate coupling part 2 comprises a base portion 21 with an axially outwardly projecting annular part 17 having an annular inwardly projecting beak 18 with a first beak surface 19 which is essentially perpendicular to the center axis C–C' or has an angle which corresponds to the angle of the recess surface 12 to the center axis C–C', and a second preferably rounded beak surface 20 which, however, in the area 20a, 20b which adjoins the annular tip 19a of the beak 18 between the first beak surface 19 and the second beak surface 20 is essentially parallel to the center axis C–C'.

The beak 18 of the plate coupling part 2 is so shaped as to be capable of engaging with the recess 11 of the bag coupling part 1, which is explained later on.

The base portion 21 of the plate coupling part 2 is in the annular area closest to the axially outwardly projecting part 17, axially thicker than the in radial direction outermost area of the base portion 21 to which the adhesive disc (not shown) is attached. This provides a stable coupling and entails reduced tendency to bending of the flange upon application, it at the same time being comparatively easy to weld the non-adhesive surface of the adhesive disc to the surface 21a of the coupling part 2.

On the in radial direction inner side of the projecting part 17 of the plate coupling 2, the coupling part 2 is provided with an annular flange 22. This flange 22 has two functions. When the plate coupling part 2 is attached around a stoma, this flange 22 will prevent faeces or other secretion from the stoma from penetrating between the adhesive plate and the plate coupling part 2. This is an important hygienic measure, since the plate coupling part 2 is often used for several days, and must consequently be kept clean. The flange 22 may further more act as an attachment rib for a convex ring which some ostomy patients have to use. As regards the latter function of the flange, the flange 22 could, however, just as well be replaced by in radial direction inwardly projecting knobs or the like for retaining a convex ring in the way it is known from e.g. the applicant's own DK patent application No. 0371/92 corresponding to WO 93/18725.

The base flange 21a may furthermore in a manner known per se be provided with not shown ears for attachment of a supporting belt.

The locking ring 3 which is intended for positioning in the groove 7 of the bag coupling part 1, as shown in FIG. 1, comprises an annular base ring 25 and an in radial direction inwardly projecting annular protrusion 26 which fits into the in radial direction innermost groove section 7a of the coupling part 1. The base ring 25 and the protrusion 26 are connected by an intermediate piece 27 which is bent so as to have an S-shaped cross-section. Hereby a slightly resilient effect is achieved between the protrusion 26 and the base ring 25, which results in a reduced demand on the manufacturing tolerances of the units. The resilient effect between the base ring 25 and the protrusion 26 may of course just as well be obtained by an intermediate piece having any other bent cross-section, e.g. having a C-shaped cross-section, or the intermediate piece may be inclined in relation to the radial direction between the base ring 25 and the protrusion 26.

From the intermediate piece 27 a first and a second guide flange 28, 29 with rounded edges project in oppositely directed axial directions. Above all, the object of these guide flanges 28, 29 is to guide the locking ring 3 during positioning thereof in groove section 7 and during locking thereof, so that the protrusion 26 is guided into the innermost groove section 7A. The first guide flange 28, which extends in axial direction towards the base portion 4 of the first coupling part 1 when the coupling is mounted, further has a fortifying effect on the seals of the coupling, which is explained in more detail below.

Figure 4:
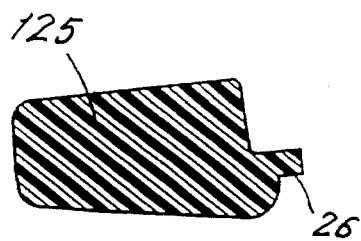
FIG. 4 is a radial section through another embodiment of a locking ring.

As shown in FIG. 4 the locking ring 3 may also be shaped without the intermediate piece 27, this locking ring consists of a base ring 125 from which a protrusion 26 corresponding to the protrusion 26 in the embodiment shown in FIGS. 1–3 projects in radial inward direction.

Figure 5:
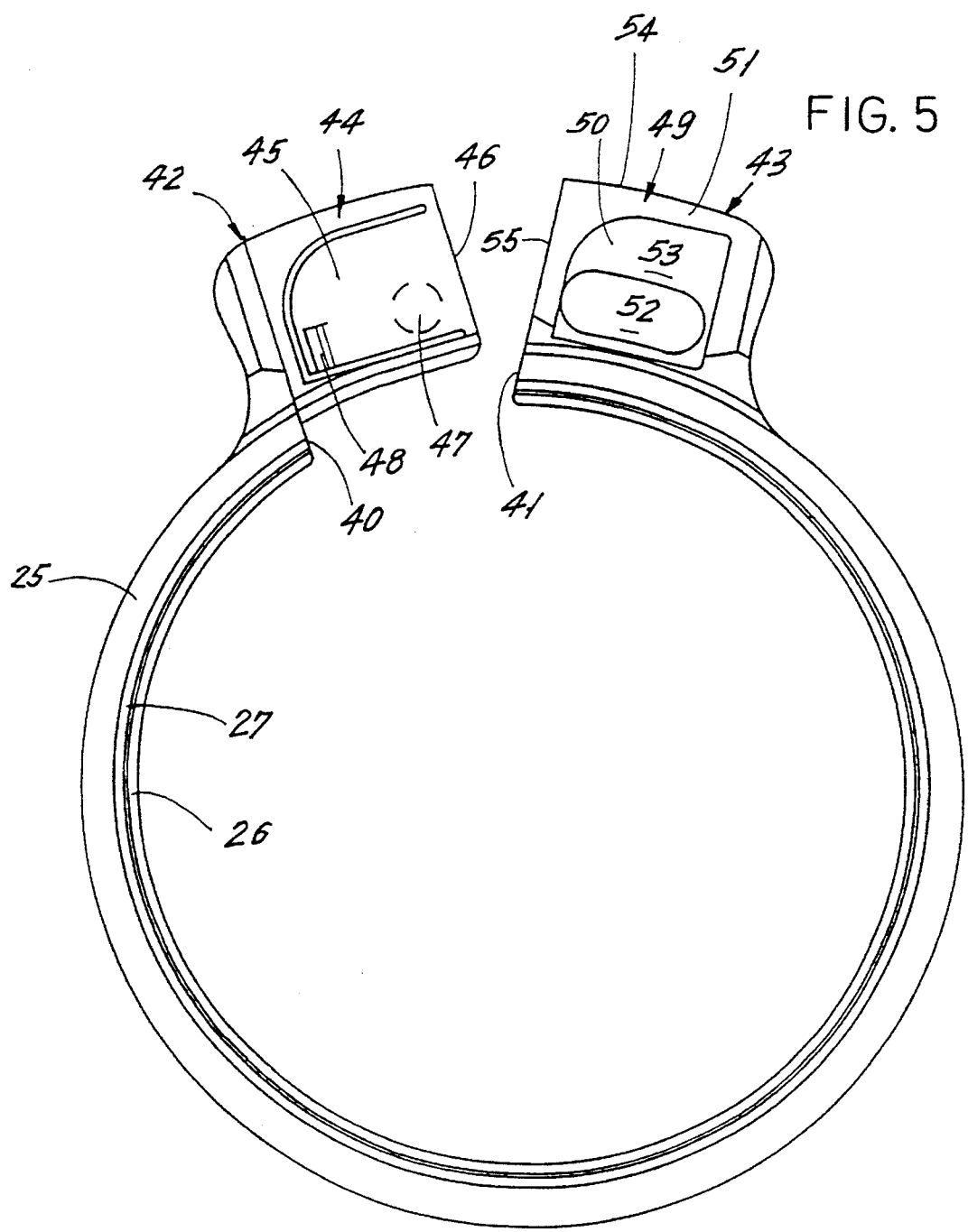
FIG. 5 shows a locking ring in open state.

The locking ring 3 may advantageously be provided with a two-step lock like those described in WO 91/01118. FIG. 5 shows a locking ring having a preferred two-step lock. The locking ring corresponds to the one shown in FIGS. 1–3, and thus consists of a base ring 25, an intermediate piece 27, and a protrusion 26. The locking ring 3 is provided with a cut for forming two ends 40, 41, being provided with a male locking unit 42 and a female locking unit 43, respectively, which may be passed into a primary and a secondary mutual engagement.

The male locking unit 42 comprises a flat disc 44 which projects radially from the locking ring 3. The flat disc 44 comprises a vane 45 which projects from the lead-in edge 46 which is first introduced into the female locking unit. From the first side of the vane 45 closest to the lead-in edge 46 a first bead 47 projects in axial direction, and from the other side of the vane 45 closest to the vane tip a second bead 48 projects in axial direction.

The female locking unit 43 comprises a flat housing 49 which also projects radially from the locking ring 3. The housing 49 has a first wall 50 and a second wall 51, each being provided with a window 52, 53. The housing 49 has an open ceiling 54 and an open front wall 55.

When locking the locking ring 3 to primary locking position the lead-in edge 46 of the male locking unit 42 is introduced through the front wall 55 of the housing 49 until the bead 47 engages with the window 52 of the first wall 5.

When locking to secondary locking position the flat disc 44 of the male locking unit 42 is pushed completely into the housing 49, until the second bead 48 engages with the window 53 in the other wall 51 of the housing 49.

When opening the secondary lock of the locking ring 3 a slight pressure is exerted on the vane 45 through the window 53, until the bead 48 slips out of the engagement with the window 53. The locking ring 3 is preferably elastically deformable at least in a section of its annular extension, so that the bead 48 by itself leaps out of the engagement with the window 53 by a slight pressure on the vane 45.

When opening the primary lock of the locking ring 3 to a separated state the flat disc 44 of the male locking unit 42 is wrung and lifted somewhat, so that the distance between the walls 50 and 51 of the housing 49 is increased, and the bead 47 escapes the first window 52, whereafter the flat disc 44 can be withdrawn completely from the housing 49.

The locking ring 3 and the first coupling part 1 may advantageously, and in the way it is shown in the preferred embodiment of the invention in FIG. 1, be so constructed that the locking ring 3 prior to mounting the coupling 1 is positioned in the groove 7 in its primary locking position, in the way it is known from the applicant's WO patent application No. 91/01119. Thus, it is particularly advantageous that the maximum inner diameter of the locking ring 3, when the locking ring 3 is in its primary locking position, is smaller than the outer diameter of the collar edge 6 of the first coupling part 1. This is significantly advantageous handling-wise, since the locking ring 3 already at the moment of sale may be positioned in the groove 7 in its primary locking position, whereby the user avoids trouble of handling a separate locking ring.

In use the plate coupling part 2 is attached in a manner known per se around a stoma. Hereafter the bag coupling part 1 is forced over the axially outwardly projecting annular part 17 of the plate coupling part 2, so that the beak 18 engages with the recess 11. The locking ring 3 may as described above in advance be positioned in the groove 7 of the bag coupling part 1 in its primary locking position, i.e. so that the radially inwardly projecting protrusion 26 does not project into the innermost groove section 7a in the annular direction of the entire groove section 7, or it may be positioned in the groove 7 after assembly of the bag coupling part 1 and the plate coupling part 2. The ostomy coupling is secondarily coupled by locking the locking ring 3, so that the protrusion 26 of the locking ring 3 projects into the innermost groove section 7a of the bag coupling 1.

FIGS. 1 and 3 show the coupling in its locked position. It is seen that the outer diameter of the beak 18 is larger than the inner diameter of the protrusion 26 of the locking ring 3. This entails that the protrusion 26 of the locking ring 3 and the beak 18 at loads which try to tear the plate coupling part 2 and the bag coupling part 1 apart will squeeze the wall part 5a of the first coupling part 1 between the recess 11 and the innermost groove section 7a, whereby the strength of the coupling will be increased. This effect is further fortified by the first recess surface 12 and the first beak surface 19 being essentially plane and perpendicular to the center axis C–C'.

To avoid significant friction between the side walls 8a and 9a and the protrusion 26 of the locking ring 3 when opening or locking it, the protrusion 26 is preferably slightly axially narrower than the groove section 7a, so that there is a small clearance between the side walls 8a, 9a and the protrusion 26 when the coupling is without load. In the embodiment shown in FIG. 3 there is thus a clearance between the side wall 8a and the protrusion 26. This clearance will in practice when the coupling is without load be distributed between the protrusion 26 and the side wall 8a, and the protrusion 26 and the side wall 9a, respectively, and further it is normally smaller than the one shown in FIG. 3.

When the coupling is loaded with a heavy load the wall section 5a and the protrusion 26 will, if there is a clearance between the side walls 8a, 9a and the protrusion 26, assume a slightly inclined position in relation to its position in the state without load, which is essentially perpendicular to the center axis C–C', so that the protrusion 26 in the area closest to the groove bottom 10 will press against the side wall 8a, and in the area at some distance from the bottom 10, where this distance depends on the clearance between the side walls 8a, 9a and the protrusion 26 in position without load, the protrusion 26 will press against the side wall 9a, whereby the above squeezing of the wall part 5a is obtained. Because of the assumption by the protrusion 26 of an inclined position, the guide flange 28 will increase its pressure against the step wall 9b, which as described above results in an improved seal.

It is seen that the beak surface 19 is somewhat wider than the recess surface 12, so that the two coupling parts 1 and 2 are only in tight physical contact in the beak/recess area, and so that between the wall part 5b of the first coupling part 1, which has the groove bottom 10 as side surface, and the second coupling part 2 there is an annular clearance 30. This results in significantly reduced demands on the production tolerances of the units and at the same time it has no impairing effect on the seal.

It is especially preferred that the annular clearance 30 has a radial width which at least in an area is smaller than the width of the side wall 8a of the innermost groove section 7a, since hereby it is prevented that the wall part 5c of the first coupling part 1 between the wall part 5b and the collar edge may pass this clearance 30, so that the beak 18 and the recess 11 pass out of engagement, even when the second coupling part 2 is of a deformable material.

The lip 15 of the bag coupling part 1 abuts against the rounded surface 20 of the beak 18 so as to form a secondary seal.

The primary seal is constituted by the contact between the sealing rib 14 and an annular narrow surface area 20b on the second surface 20 of the beak 18, which is positioned at a distance from the tip 19a of the beak 18. It is particularly advantageous that this narrow sealing surface area 20b is not constituted by nor comprises the tip 19 of the beak 18, since this tip 19 may easily be damaged in use or in the production, and that this would place tremendously severe demands on manufacturing tolerances of the units. On both sides of the contact area, also designated the sealing surface, between the sealing rib 14 and the surface area 20b, there is an annular clearance 31, 32. This results in a very safe and tight contact between the beak 18 and the recess 11 in the sealing surface area. This effect is further fortified by the annular guide flange 28 of the locking ring 3 abutting tightly against the step wall 9b in an outermost surface area 28a of the guide flange 28.

Thereby the guide flange 28 also has a fortifying effect on the secondary seal between the lip 15 and the beak surface 20.

It is seen that the wider the flange 28, and the more extreme in the axial direction of the flange the contact surface between this flange 28 and the step wall 9b is positioned, the greater the seal improving effect of the flange 28 on the secondary seal. Since the maximum width of the flange 28 is limited by the axial height of the step wall 9b, it is thus advantageous to have one step as opposed to several steps, as mentioned above.

The surface area 28a of the guide flange 28, which area abuts tightly against the step wall 9b, is advantageously and as shown in the preferred embodiment of the invention, in particular FIG. 3, positioned in the same plane perpendicularly to the center axis C–C' as the annular clearance 31 between the sealing surface which constitutes the primary seal and the sealing surface which constitutes the secondary seal. Hereby it is achieved that the guide flange 28 also has a fortifying effect on the primary seal.

The protrusion 26 of the locking ring 3 abuts against the side wall 9a of the innermost groove section 7a and the larger the load, the more the pressure of the flange 28 against the step wall 9b is increased, whereby the seals, both the primary and the secondary, are improved.

When the bag coupling is to be removed, the locking ring 3 is first opened to its primary locking position as previously described. Hereafter the bag coupling part 1 may easily be removed by a pull in the pulling flap.

The locking ring 3 and the plate coupling part 2 may advantageously be made of a rigid or semi-rigid polymeric material. The rigidity of the bag coupling part 1 has no significant influence on the coupling strength, since this part is rigidly retained between the plate coupling part 2 and the locking ring 3. In view of the primary coupling together, i.e. forcing the bag coupling part 1 over the plate coupling part 2, until the beak 18 and recess 11 engage, a softer and consequently more flexible material is, however, preferred.

For all the parts it is, however, preferred to use moldable and in particular injection moldable material, and further it is preferred that the bag coupling material and the plate coupling material are weldable to bag/plug or adhesive disc, respectively.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An ostomy coupling comprising:

a first and a second annular coupling part; and a locking ring for locking together the two coupling parts, each of the two coupling parts having an attachment surface for attaching a part associated with the corresponding coupling part, the first coupling part comprising:

a collar having a radially outwardly projecting annular edge, the edge defining a groove with an in radial direction innermost groove section, and an annular recess positioned in the radial direction inner side of the collar, the second coupling part comprising:

an axially projecting part having an annular radially outwardly projecting beak, the beak being structured and arranged on the second coupling part so as to engage the annular recess in the first coupling part when the first coupling part is positioned around the second coupling part, and the locking ring having an annular in the radial direction inwardly projecting protrusion, and the locking ring is positioned in the groove of the first coupling part, wherein when the locking ring is in a locked position with respect to the first and second coupling parts, an innermost diameter of the locking ring is smaller than a largest diameter of the beak of the second coupling part, and the annular recess at the inner side of the first coupling part is closer to the attachment surface of the first coupling part than the groove section of the first coupling part.

2. An ostomy coupling according to claim 1, wherein the associated part of the first coupling part is one of a collection receptacle and a closing plug, and the associated part of the second coupling part is an adhesive disc.

3. An ostomy coupling according to claim 1, wherein the groove section of the groove in the first coupling part has a width in the radial outward direction that is less than the width of remaining portions of the groove in the radial outward direction.

4. An ostomy coupling according to claim 1, wherein the recess in the first coupling part has a first and a second surface, the first surface being at a greater distance from the attachment surface of the first coupling part than the second surface, and the first surface being essentially planar and perpendicular to a center axis C–C' of the first coupling part, the beak having a first and a second surface, the first surface of the beak being closer to the attachment surface of the second coupling part than the second surface of the beak, and the second surface of the beak is also essentially planar and perpendicular to the center axis C–C'.

5. An ostomy coupling according to claim 1, further comprising an annular sealing surface between the recess of the first coupling part and the beak of the second coupling part, the sealing surface at both sides being enclosed by annular clearances between the beak and the recess.

6. An ostomy coupling according to claim 1, wherein the locking ring further includes an intermediate piece which projects radially outward from the annular protrusion.

7. An ostomy coupling according to claim 1, wherein the locking ring has a two-step lock such that the locking ring is lockable in a first step so as not to exceed a first large inner diameter and in a second step so as to be retained in a smaller inner diameter, the smaller inner diameter essentially corresponding to the diameter of a bottom wall of the groove in the first coupling part.

8. An ostomy coupling according to claim 7, wherein the first large inner diameter of the locking ring is smaller than an outer diameter of the collar edge of the first coupling part.

9. An ostomy coupling according to claim 1, wherein the first coupling part is provided with a pulling flap.

10. An ostomy coupling according to claim 1, wherein the groove in the first coupling part has a bottom and a wall part of the first coupling part having the bottom of the groove as a side surface, and the groove section has a side wall,
a clearance between the wall part of the first coupling part and the second coupling part has a radial width which at least in an area is smaller than a width of the side wall of the groove section, which side wall faces the beak when the coupling is mounted.

11. An ostomy coupling according to claim 2, wherein the groove in the first coupling part expands width-wise in the radial outward direction in at least one step.

12. An ostomy coupling according to claim 5, wherein the sealing surface is positioned at a predetermined distance from a tip of the beak.

13. An ostomy coupling according to claim 12, wherein the beak has a first and a second surface, and the sealing surface includes an annular sealing rib on the recess of the first coupling part and an annular surface area on one of the surfaces of the beak, the one of the surfaces of the beak in an area adjoining the tip of the beak is not in direct contact with the first coupling part.

14. An ostomy coupling according to claim 6, wherein the intermediate piece is generally S-shaped in section.

15. An ostomy coupling according to claim 9, wherein the pulling flap is located at the edge of the first coupling part.

16. An ostomy coupling comprising:

a first and a second annular coupling part; and a locking ring for locking together the two coupling parts, each of the two coupling parts having an attachment surface for attaching a part associated with the corresponding coupling part, the first coupling part comprising:

a collar having an edge, the edge defining a groove with a groove section at an inner portion of the groove, and an annular recess provided at an inner side of the collar, the second coupling part comprising:

a projecting part having an annular beak, the beak being structured and arranged on the second coupling part so as to engage the annular recess in the first coupling part when the first coupling part is positioned around the second coupling part, and the locking ring having a protrusion, wherein when the locking ring is in a locked position with respect to the first and second coupling parts, an innermost diameter of the locking ring is smaller than a largest diameter of the beak of the second coupling part, and the annular recess of the first coupling part is closer to the attachment surface of the first coupling part than the groove section of the first coupling part.

17. An ostomy coupling according to claim 16, wherein the edge of the first coupling part is annular in shape and projects outwardly in a radial direction from the collar, and the annular recess is positioned in a radially inner side of the collar; the annular beak of the second coupling part projects outwardly in a radial direction from the axially projecting part; and the protrusion of the locking ring is annular in shape and projects inwardly in a radial direction.

18. An ostomy coupling according to claim 16, wherein at least one step is formed between the groove in the first coupling part and the groove section such that the groove section has a width less than the width of the groove.

* * * * *